United States Patent [19]

Braid

[11] 4,125,472
[45] Nov. 14, 1978

[54] LUBRICANT COMPOSITIONS

[75] Inventor: Milton Braid, Westmont, N.J.

[73] Assignee: Mobil Oil Corporation, New York, N.Y.

[21] Appl. No.: 859,406

[22] Filed: Dec. 12, 1977

Related U.S. Application Data

[63] Continuation-in-part of Ser. No. 733,580, Oct. 18, 1976, abandoned.

[51] Int. Cl.² ............... C10M 1/44; C10M 3/48; C07D 233/04; C07D 235/00
[52] U.S. Cl. .................................. 252/32.5; 44/63; 548/347
[58] Field of Search ............... 252/32.5; 548/347; 44/63

[56] References Cited

U.S. PATENT DOCUMENTS 4,052,324  10/1977  Braid .................. 252/32.5

Primary Examiner—Irving Vaughn
Attorney, Agent, or Firm—Charles A. Huggett; Raymond W. Barclay; Thomas S. Szatkowski

[57] ABSTRACT

Lubricant compositions are provided which contain: oleaginous media, and an antiwear improving amount of a product formed by reacting (a) a compound having the formula:

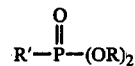

where R' is a substantially unbranched paraffinic alkyl group containing from about 10 to about 36 carbon atoms, and R is a hydrocarbyl group containing from 1 to about 4 carbon atoms with at least one hydrogen atom present on the carbon atom which is bonded to the oxygen; with (b) a substituted imidazoline of the formula:

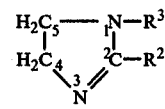

where one of the $R^2$ and $R^3$ substituents must be a substantially unbranched paraffinic or olefinic hydrocarbyl group containing from about 12 to about 35 carbon atoms; and the other $R^2$ or $R^3$ substituent is selected from the group consisting of: paraffinic alkyl containing from 1 to about 35 carbon atoms, alkenyl containing from 1 to about 35 carbon atoms, and hydroxy-, alkoxy-, alkoxymethoxy-, and oxo-substituted alkyl and alkenyl containing from 1 to about 20 carbon atoms; at proportions which are most preferably stoichiometric and at temperatures greater than 150° C. Particularly contemplated are compositions in the form of lubricating oils and greases.

21 Claims, No Drawings

LUBRICANT COMPOSITIONS

CROSS REFERENCE TO RELATED APPLICATION

This application is a continuation-in-part of application Ser. No. 733,580, filed Oct. 18, 1976 now abandoned.

BACKGROUND OF THE INVENTION

1. Field of the Invention

Farm, off-highway construction equipment and industrial tractors, especially those units employing a common fluid reservoir, presently use multifunctional lubricants. These lubricants are considered multifunctional because they must meet the requirements of the transmissions, differentials, final drives, hydrostatic transmissions, hydraulic systems, power steering systems, and fluid immersed disk brakes of the specialized equipment. Thus, for a lubricant to be considered for use in such equipment, it should desirably contain the following properties: oxidative and hydrolytic stability, good antiwear qualities, and compatibility with other lubricant compositions.

In addition, friction modifying characteristics are very important to assure proper, decisive operation of multidisc transmission clutches and oil immersed brake discs. Water tolerance characteristics are especially important in friction modified lubricants for maintaining the performance integrity of the lubricant in the presence of water formed or introduced during operation.

This invention relates to lubricant compositions, which may be in the form of fuels, heat exchange fluids, lubricating oils or greases thereof, which possess improved water tolerance, friction modifying, antiwear, and antichatter properties. Such compositions are contemplated as being suitable for use in the specilized equipment described hereinabove.

2. Description of the Prior Art

British Pat. No. 1,247,541 discloses lubricant compositions containing alkanephosphonates as having friction modifying characteristics. The alkanephosphonates described therein have the formula:

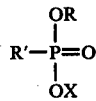

where R is methyl or ethyl, R' is a straight chain alkyl having 12 to 20 carbon atoms and X is a methyl, ammonium, alkylammonium or alkenylammonium group, the organic X group having from 1 to 30 carbon atoms. These compounds may be produced as follows:

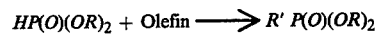

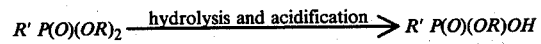

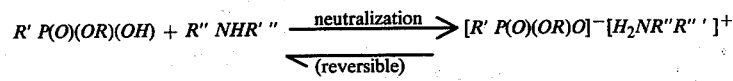

where R and R' are defined above and, R" and R''' are each alkyl or alkenyl of 1 to 30 carbon atoms.

In reaction (1), a dialkyl phosphonate is reacted with an olefin to produce a R' substituted dialkyl phosphonate. This product is partially hydrolyzed in step (2) by treatment with a base followed by acidification to produce an R' substituted monoalkyl acid phosphonate, which may be further reacted with an amine to form the corresponding salt by acid-base neutralization reaction (3) with a transfer of the acid hydrogen. An acid-base neutralization reaction involving a proton transfer, for example: $HA + R_2NH \rightleftharpoons A^- + R_2N^+H_2$ is reversible. If the equilibrium is destroyed such as by distillation of the acid or amine, the original reactants can be recovered. This is not true of the displacement reaction products of the present invention. Due to the reversibility of reaction (3) the salt products of the British patent may actually contain some acid phosphonate. Such compounds are sources of "reserve" acidity and tend to "deactivate" basic components of lubricant compositions by neutralization. It is further noted that the hydrolysis and acidification reactions of step (2) are very corrosive and, in addition, present problems with regard to emulsions, exotherms, solvents, solvent recovery, and comprise a multistep process.

In U.S. Pat. No. 3,793,199 an alkanephosphonate diester is reacted with a non-cyclic amine at temperatures of from 80° C. to 150° C., with 90°–130° C. being preferred, according to the following formula:

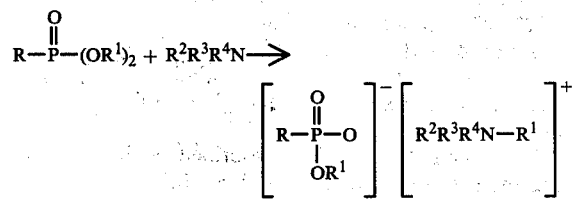

where R is a substantially straight chain aliphatic radical having from about 11 to 40 carbon atoms, $R^1$ is a lower aliphatic radical having from one to eight carbon atoms, $R^2$ is a hydrocarbyl radical having from one to 40 carbon atoms and $R^3$ and $R^4$ are hydrogen, a hydrocarbyl radical having from one to 40 carbon atoms or a substituted hydrocarbyl radical having amino, alkylamino or hydroxy functional groups.

When $R^3$ and $R^4$ are hydrogen, a reversible acid-base reaction may occur. For example, if $R^3$ were hydrogen, the following reversible acid-base type reaction:

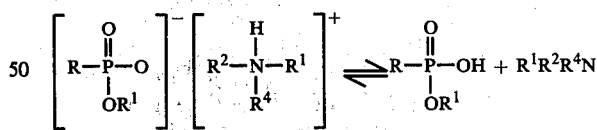

would cause the production of acid phosphonate. The detrimental effect of the presence of acid phosphonate in a lubricant composition has already been discussed.

Since the present invention utilizes imidazolines having no hydrogen connection to the nitrogen atoms, such undesirable reactions cannot occur.

In South African Pat. No. 74/4882, there is described a lubricant composition which contains a salt of (a) an amine or an imidazoline which contains a straight chain aliphatic group of 12 to 22 carbon atoms and (B) an alkyl, long chain alkyl ($C_{12}$–$C_{22}$) acid phosphonate.

In U.S. Pat. No. 2,706,194, compounds of the formula

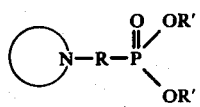

are described. These compounds are synthesized at temperatures from about 25° C. to about 150° C., and differ greatly from the products of the present invention in that the products of the present invention do not have a hetorocyclic ring which containing nitrogen and carbon, attached directly to the phosphorus atom. Also, as will be described in more detail hereinafter, it is essential that the products of the present inventions be formed at temperatures greater than 150° C.

In U.S. Pat. Nos. 3,711,404, 3,846,317, 3,677,943 and 3,227,727 compounds in which a nitrogen moiety is attached directly to a phosphorus atom are disclosed. The products of the present invention do not contain any direct connection between phosphorus and nitrogen.

It is noted that products described in the prior art, and the methods, reactants, and conditions for producing them are different from those of the present invention, as will be described presently.

SUMMARY OF THE INVENTION

It has now been found that an improvement in the antiwear and friction modifying properties of a lubricant can be obtained by incorporating therein a product formed by reacting:

(a) a dialkyl alkane phosphonate having the formula:

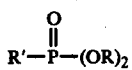

where R' is a substantially unbranched paraffinic alkyl group containing from about 10 to about 36 carbon atoms, but preferably is a substantially unbranched paraffinic alkyl group containing from about 10 to about 20 carbon atoms, and most preferably is octadecyl; and R is a hydrocarbyl group containing from 1 to about 4 carbon atoms with at least one hydrogen atom present on the carbon atom which is bonded to oxygen, but R preferably is methyl or ethyl and most preferably is methyl; with (b) a substituted imidazoline of the formula:

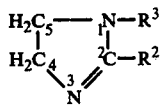

where one of the $R^2$ and $R^3$ substituents must be a substantially unbranched paraffinic or olefinic hydrocarbyl group containing from about 12 to about 35 carbon atoms; and the other $R^2$ or $R^3$ substituent is selected from the group consisting of: paraffinic alkyl containing from 1 to about 35 carbon atoms, alkenyl, containing from 1 to about 35 carbon atoms, and hydroxyalkoxy-, alkoxymethoxy-, and oxo-substituted alkyl and alkenyl containing from 1 to about 20 carbon atoms.

It is preferred that $R^2$ be a substantially unbranched paraffin or olefin hydrocarbyl group containing from 12 to about 35 carbon atoms, and most preferred that $R^2$ be a substantially unbranched alkenyl group containing from about 13 to about 21 carbon atoms; with an alkenyl group containing 17 carbon atoms being the most particularly preferred group.

The preferred $R^3$ substituent is an alkyl group containing 1 to 20 carbon atoms, which most preferably is substituted with a hydroxy, alkoxy, alkoxymethoxy or oxo group. Of these, the particularly preferred substituent is a hydroxy substituted straight chain alkyl group containing from 2 to about 4 carbon atoms, with the —$CH_2CH_2OH$ group being the most particularly preferred.

Non-limiting examples of the phosphonate compounds suitable for use herein include: dimethyl, diethyl, diisopropyl, di-n-propyl, dibutyl, di-isobutyl and di-sec-butyl decylphosphonate; dimethyl, diethyl, diisopropyl, di-n-propyl, dibutyl, di-isobutyl and di-sec-butyl dodecylphosphonate; dimethyl, diethyl, diisopropyl, di-n-propyl, dibutyl, di-isobutyl and di-sec-butyl tetradecylphosphonate; dimethyl, diethyl, diisopropyl, di-n-propyl, dibutyl, di-isobutyl and di-sec-butyl hexadecylphosphonate; dimethyl, diethyl, diisopropyl, di-n-propyl, dibutyl, di-isobutyl and di-sec-butyl heptadecylphosphonate; dimethyl, diethyl, diisopropyl, di-n-propyl, dibutyl di-isobutyl and di-sec-butyl octadecylphosphonate; and dimethyl, diethyl, diisopropyl, di-n-propyl, dibutyl, di-isobutyl and di-sec-butyl cosanylphosphonate.

Non-limiting examples of the imidazoline compounds suitable for use herein include: 1-(2-hydroxycosanyl)-2-methylimidazoline, 1-(2-hydroxybutyl)-2-undecenylimidazoline, 1-(2-hydroxyhexyl)-2-tetradecylimidaoline, 1-(2-hydroxypropyl)-2-hexdecylimidazoline, 1-(2-hydroxyethyl)-2-heptadecenylimidazoline, 1-(2-hydroxyethyl)-2-octadecylimidazoline, 1-(2-hydroxyethyl)-2-dodecenylimidazoline, 1-(2-hydroxyoctadecyl)-2-heptadecylimidazoline, and 1-methyl-2-octadecenylimidazoline.

The imidazoline compounds may be prepared by reaction of appropriately substituted 1,2-diaminoethanes with alkylcarboxylic acids as described in U.S. Pat. No. 2,267,965. A particularly preferred acid is oleic acid. Imidazolines which include examples of the above cited compounds are items of commerce as, for example, Amine C, Amine O and Amine S marketed by the Ciba-Geigy Corporation.

The imidazoline may be reacted with the phosphonate in proportions such that there is an excess of imidazoline, however, preferably they are reacted in a molar ratio of imidazoline to phosphonate of 1.2:1 and most preferably are reacted in stoichiometric proportions. Thus, the phosphonate is reacted with at least the stoichiometric amount of the imidazoline, and preferably from about 1:1 to about 1.2:1 molar ratio of imidazoline to phosphonate.

The reaction is conducted at a temperature greater than 150° C., however, it is preferably to use temperatures from about 160° C. to about 210° C.; while temperatures from about 170° C. to about 190° C. are most preferred. It is essential that temperatures greater than 150° C. be used, since products made by reaction at lesser temperatures do not provide the requisite improvement in water tolerance properties as will be shown hereinafter.

Reaction times may vary from 4 hours to as little as about 0.25 with shorter reaction times applicable at higher reaction temperatures. Heating may be done at reduced pressure or at atmospheric pressure. Using an inert atmosphere, such as nitrogen or carbon dioxide to avoid oxidative degradation during processing may be advantageous.

Spectroscopic analysis of the reaction products of the instant invention by C-13 NMR shows that one R group of the dialkylalkane phosphonate attaches to the nitrogen in the 1-position of the imidazoline forming a quaternary amine. The irreversibility of this reaction has already been discussed.

The reaction may be illustrated as follows:

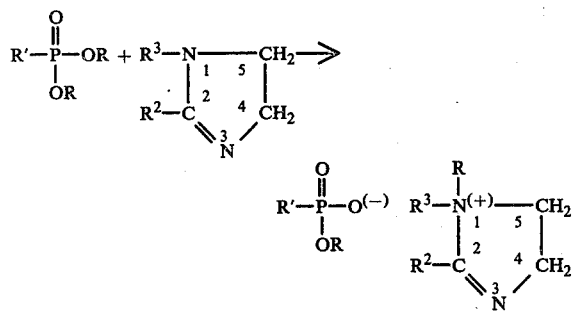

It is contemplated incorporating anti-wear or antistatic friction improving amounts of the aforementioned reaction product in base oleaginous media. In this regard, from about 0.001 to about 7 percent, by weight, preferably from about 0.25 to about 1, and for many applications, from about 0.4 to 0.75 percent by weight may be incorporated into the base oleaginous media.

The oleaginous media may comprise any materials that normally exhibit insufficient anti-wear properties or which require friction modifying characteristics. A field of specific applicability is the improvement of oleaginous media which may be selected from the group consisting of lubricating oils, greases, fuels, heat exchange fluids, hydraulic and other functional fluids. Of particular significance is the improvement in lubricating media which may comprise lubricating oils, in the form of either a mineral oil or a synthetic oil, or in the form of a grease in which any of the aforementioned oils are employed as a vehicle. In general, mineral oils, both paraffinic, naphthenic and mixtures thereof, employed as the lubricant, or grease vehicle, may be of any suitable lubricating viscosity range, as for example, from about 45 SSU at 100° F. to about 6000 SSU at 100° F., and preferably, from about 50 to about 250 SSU at 210° F. These oils may have viscosity indexes varying from below zero to about 100 or higher. Viscosity indexes from about 70 to about 95 are preferred. Where the lubricant is to be employed in the form of a grease, the lubricating oil is generally employed in an amount sufficient to balance the total grease composition, after accounting for the desired quantity of the thickening agent, and other additive components to be included in the grease formulation. A wide variety of materials may be employed as thickening or gelling agents. These may include any of the conventional metal salts or soaps, which are dispersed in the lubricating vehicle in grease-forming quantities in such degree as to impart to the resulting grease composition the desired consistency. Other thickening agents that may be employed in the grease formulation may comprise the non-soap thickeners, such as surface-modified clays and silicas, polyaryl ureas, calcium complexes and similar materials. In general, grease thickeners may be employed which do not melt and dissolve when used at the required temperature within a particular environment; however, in all other respects any material which is normally employed for thickening or gelling hydrocarbon fluids for forming grease can be used in preparing the aforementioned improved grease in accordance with the present invention.

In instances where synthetic oils, or synthetic oils employed as the vehicle for the grease, are desired in preference to mineral oils, or in combination therewith, various compounds of this type may be successfully utilized. Typical synthetic vehicles include polyisobutylene, polybutenes, hydrogenated polydecenes, polypropylene glycol, polyethylene glycol, timethylol propane esters, neopentyl and pentaerythritol esters, di(2-ethylhexyl)sebacate, di-(2-ethylhexyl)adipate, dibutyl phthalate, fluorocarbons, silicate esters, silanes, esters of phosphorous-containing acids, liquid ureas, liquid or fluid ferrocene derivatives, hydrogenated mineral oils, chain-type polyphenyl, siloxanes and silicones (polysiloxanes), alkyl-substituted diphenyl ethers typified by a butyl-substituted bis (p-phenoxy phenyl) ether, phenoxy phenylethers, etc.

Of still further significance is the friction modifying improvement in petroleum distillate fuel oils having an initial boiling point from about 75° F. to about 135° F. and an end boiling point from about 250° F. to about 750° F. It should be noted, in this respect, that the term "distillate fuel oils" is not intended to be restricted to straight-run distillate fractions. These distillate fuel oils can be straight-run distillate fuel oils, catalytically or thermally cracked (including hydrocracked) distillate fuel oils, naphthas and the like, with cracked distillate stocks. Moreover, such fuel oils can be treated in accordance with well-known commercial methods, such as acid or caustic treatment, hydrogenation, solvent-refining, clay treatment and the like.

The distillate fuel oils are characterized by their relatively low viscosity, pour point and the like. The principal property which characterizes these hydrocarbons, however, is their distillation range. As hereinbefore indicated, this range will lie between about 75° F. and about 750° F. Obviously, the distillation range of each individual fuel oil will cover a narrower boiling range, falling nevertheless within the above-specified limits. Likewise, each fuel oil will boil substantially, continuously throughout its distillation range.

Particularly contemplated among the fuel oils are Nos. 1, 2 and 3 fuel oils, used in heating and as diesel fuel oils, gasoline, turbine oil and jet combustion fuels. The fuel oils generally conform to the specification set forth in ASTM Specification D396-48T. Specifications for diesel fuels are defined in ASTM Specification D975-48T. Typical jet fuels are defined in Military Specification MIL-F-5624B.

The mineral oil heat-exchange fluids particularly contemplated in accordance with the present invention have the following characteristics: high thermal stability, high initial boiling point, low viscosity, high heat-carrying ability and low corrosion tendency.

Further, the transmission fluids of consequence to the present invention are blends of highly refined petroleum base oils combined with VI improvers, detergents, defoamants and special additives to provide lubricity characteristics. Varied transmission design concepts have led to the need for fluids with markedly different frictional characteristics, so that a single fluid cannot satisfy all requirements. The fluids intended for use in passenger car and light-duty truck automatic transmissions are defined in the ASTM Research Report D-2: RR 1005 on "Automatic Transmission Fluid/Power Transmission Fluid Property and Performance Definitions". Specifications for low-temperature and aircraft fluids are defined in U.S. Government Specification MIL-H-5606A.

It is to be understood, however, that the compositions contemplated herein can also contain other materials. For example, corrosion inhibitors, detergents, extreme pressure agents, viscosity index agents, antioxidants, antiwear agents and the like can be used. These materials do not detract from the value of the compositions of this invention, rather these materials serve to impart their customary properties to the particular compositions in which they are incorporated.

DESCRIPTION OF SPECIFIC EMBODIMENTS

The following data and examples will serve to illustrate the novel products of the present invention and their efficacy as lubricant improvers in the antiwear and friction modifying characteristics of lubricant compositions. The criticality of reacting at a temperature greater than 150° C. will also be shown. It will be understood, however, that it is not intended the invention be limited to the particular additives as described and that various modifications thereof can be employed as will be readily apparent to those skilled in the art.

EXAMPLE 1

A solution of 35 g of dimethyl octadecylphosphonate and 35 g of 1-(2hydroxyethyl)-2-heptadecenylimidazoline in 400 ml of petroleum ether b.p. 30°–60° C. was chemically dried with anhydrous calcium sulfate. The petroleum ether was removed by distillation and the temperature of the homogeneous residue was raised to 150° C. and maintained for 1.5 hr under reduced pressure of about 200 mm of Hg while a slow stream of nitrogen was passed through subsurface. The reaction product was obtained as an amber, very viscous semi-oil.

EXAMPLE 2

As in Example 1, a mixture of 5 g of dimethyl octadecylphosphonate and 5 g of 1-(2-hydroxyethyl)-2-heptadecenylimidazoline was heated for 1.5 hours at 150° C. at a reduced pressure of less than 0.1 mm of mercury. The product was an amber, very soft semisolid.

EXAMPLE 3

Under an atmosphere of nitrogen, 2.9 of dimethyl octadecylphosphonate and 2.9 g of 1-(2-hydroxymethyl)-2-heptadecenylimidazoline was heated together for 2 hours at 130°–140° C. The resulting product was an amber, soft solid.

EXAMPLE 4

As in Example 3, a mixture of 2 g of 1-(2-hydroxyethyl)-2-heptadecenylimidazoline and 2 g of dimethyl octadecylphosphonate was heated at atmospheric pressure under nitrogen for 2 hours. The product was an amber, soft semisolid.

EXAMPLE 5

A mixture of 25 g of dimethyl octadecylphosphonate and 25 g of 1-(2-hydroxyethyl)-2-heptadecenylimidazoline was heated at 170° C. for about 2 hours under a pressure of less than 1 mm of mercury while a very slow stream of nitrogen was passed through the mixture. The residue after cooling was an amber, very soft, waxy solid, 47.8 g.

EXAMPLE 6

An aliquot portion of the product of Example 1 was heated in an atmosphere of nitrogen under a reduced pressure of less than 1 mm Hg of mercury at a temperature of 200° C. for 0.5 hr. The product produced by this treatment was slightly darker in color and slightly more viscous than the product of Example 1.

EXAMPLE 7

A mixture of 3.6 g of dimethyloctadecylphosphonate and 3.6 g of 1-(2-hydroxyethyl)-2-heptadecenylimidazoline was heated under nitrogen for 1 hour at 110° C. The infrared spectrum of the resulting product was essentially the same as that of the residue remaining after cyclohexane is evaporated at room temperature from a solution containing equal weights of the above reactants. This spectrum differs substantially from those of the products obtained in Examples 1–6 where the reactants have been heated at 130° C. and higher.

EXAMPLE 8

A mixture of 31 g of dimethyl tetradecylphosphonate and 35 g of 1-(2-hydroxyethyl)-2-heptadecenylimidazoline is heated for 2 hours at 190° C. under pressure of about 200 mm of Hg. Upon cooling there is obtained an amber, viscous semisolid product.

EXAMPLE 9

A mixture of 35 g of dimethyl octadecylphosphonate and 36 g of 1-(2-hydroxyoctadecenyl)-2-methylimidazoline is heated at 180° C. for 2.5 hours under reduced pressure of less than 0.5 mm of mercury with air excluded. After cooling, the product is obtained as a very soft solid.

EXAMPLE 10

As in Example 2, 39 g of diethyl octadecylphosphonate and 41 g of 1-(2-hydroxyethyl)-2-heptadecylimidazoline are heated together under nitrogen under less than 1 mm of mercury pressure at a temperature of 170° C. for about 2 hours to afford a light amber, waxy solid product.

EXAMPLE 11

To 45 g of dibutyl octadecylphosphonate heated at 190° C. under nitrogen there is added while stirring 35 g of 1-methyl-2-heptadecenylimidazoline. Pressure is reduced to 50 mm of mercury while the temperature is maintained for 2 hours. The resulting product is a very viscous orange oil.

EXAMPLE 12

A mixture of 35 g of dimethyl octadecylphosphonate and 40 g of the imidazoline prepared from the reaction of N-betahydroxyethylethylenediamine and behenic acid, 1-(2-hydroxyethyl)-2-eicosanylimidazoline, is stirred under nitrogen for 2.5 hours while heating at 195° C. The reaction product is obtained as a yellowish waxy solid.

Compositions containing 0.5 weight percent of the production of Examples 1–6 and 99.5 weight percent of a base oil were tested for water tolerance, anti-wear and chatter characteristics.

The International Harvester Water Tolerance Test is fully described in the International Harvester Engineering Materials Specification, as Engineering Research Test Method BT-7. In this test, the clearness or turbidity of the compositions after water has been added is the critical property.

The standard Shell Four Ball Wear Test is described in U.S. Pat. No. 3,423,316. In general, three steel balls of SAE 52-100 steel are held in a ball cup. A fourth ball, positioned on a rotatable vertical axis, is brought into contact with the three balls and is rotated against them. The force with which the fourth ball is held against the three stationary balls is varied according to the desired load. The test composition is added to the ball cup and acts as a lubricant for the rotation. At the end of the test, the steel balls are investigated for wear-scar; the extent of scarring represents the effectiveness of the lubricant as an anti-wear agent.

The Timken EP Test utilizes a hardened steel ring which is rotated against another steel test block while the test lubricant is fed the point of contact between the ring and block. This test and its use is described in SAE Reference Paper No. 680607.

The John Deere Tractor Chatter Index Test is fully described in U.S. Pat. No. 3,652,410.

The test results are reported in the following table:

(a) a dialkyl alkane phosphonate compound having the formula

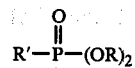

where R' is a substantially unbranched paraffinic alkyl group containing from about 10 to about 36 carbon atoms and R is a hydrocarbyl group containing from 1 to about 4 carbon atoms with at least one hydrogen atom present on the carbon atom which is bonded to the oxygen; with at least the stoichiometric amount of (b) a substituted imidazoline of the formula:

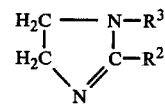

where one of the $R^2$ and $R^3$ substituents must be a substantially unbranched paraffinic or olefinic hydrocarbyl group containing from about 12 to about 35 carbon atoms; and the other $R^2$ or $R^3$ substituent is selected from the group consisting of: paraffinic alkyl containing from 1 to about 35 carbon atoms, alkenyl containing from 1 to about 35 carbon atoms and hydroxy-, alkoxy-, alkoxymethoxy-, and oxo-substituted alkyl and alkenyl containing from 1 to about 20 carbon atoms.

2. The composition of claim 1 wherein the reaction product is present in an amount from about 0.001% to about 7% by weight.

3. The composition of claim 1 wherein the reaction product is present in an amount from about 0.25% to about 1% by weight.

4. The composition of claim 1 wherein the reaction product is present in an amount from about 0.4% to about 0.75%.

5. The composition of claim 1 wherein said oleagi-

TABLE I

| Formulation: | | | | Internation Harvester Water Tolerance Test | | Shell Four Ball Wear Test Wear Scar | John Deere Chatter Test | | Timken EP Test |
|---|---|---|---|---|---|---|---|---|---|
| | | | | Haze Observed, Duplicate Runs | Rating | Diameter, mm | Chatter Index | Rating | Weight Loss, mg |
| Base Oil | — | | | — | — | — | — | — | — |
| Base Oil | + 0.5 Wt % | Example | 1 Prod | Heavy/Heavy | Unsatisfactory | — | — | — | — |
| " | " | " | 2 " | Heavy/Heavy | Unsatisfactory | — | — | — | — |
| " | " | " | 3 " | Very Heavy/Heavy | Unsatisfactory | — | — | — | — |
| " | " | " | 4 " | Heavy/Heavy | Unsatisfactory | — | — | — | — |
| " | " | " | 5 " | Trace/Medium | Satisfactory | .425 | 170 | Pass | 16 |
| " | " | " | 6 " | Light/Medium | Satisfactory | — | — | — | — |

Thus, it is seen from the data presented in Table 1 that the products of the present invention, represented by Example 5 and 6 impart effective antiwear and water tolerance properties to the base oil. It is noted that the products made from reaction at temperatures up to and including 150° C. fail in the same regard. Thus, the criticality of the greater than 150° C. temperature requirement is shown.

I claim:

1. A lubricant composition which comprises: an oleaginous media; and an antiwear improving amount of the product formed by reacting, at a temperature greater than 150° C., nous media comprises a mineral oil.

6. The composition of claim 1 wherein said oleaginous media comprises a synthetic oil.

7. The composition of claim 1 wherein the reaction temperature is between from about 160° C. to about 210° C.

8. The composition of claim 1 wherein the reaction temperature is between from about 170° C. to about 190° C.

9. The composition of claim 1 wherein the (a) and (b) compounds are reacted in stoichiometric proportions.

10. The composition of claim 1 wherein R is an unbranched paraffinic group containing from about 10 to about 20 carbon atoms and R' is selected from the group consisting of methyl and ethyl.

11. The composition of claim 1 wherein the phosphonate compound of (a) is dimethyl octadecyl phosphonate.

12. The composition of claim 1 wherein $R^2$ is a substantially unbranched alkenyl group containing from about 13 to about 21 carbon atoms and $R^3$ is a hydroxy substituted straight chain alkyl group containing from 2 to about 4 carbon atoms.

13. The composition of claim 1 wherein the imidazoline compound of (b) is 1-(2-hydroxy ethyl)-2-heptadecenyl imidazoline.

14. A product formed by reacting, at a temperature greater than 150° C., (a) a dialkyl alkane phosphonate compound having the formula

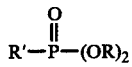

where R' is a substantially unbranched paraffinic alkyl group containing from about 10 to about 36 carbon atoms and R is a hydrocarbyl group containing from 1 to about 4 carbon atoms with at least one hydrogen atom present on the carbon atom which is bonded to the oxygen; with at least the stoichiometric amount of (b) a substituted imidazoline of the formula:

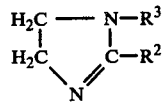

where one of the $R^2$ and $R^3$ substituents must be a substantially unbranched paraffinic or olefinic hydrocarbyl group containing from about 12 to about 35 carbon atoms; and the other $R^2$ or $R^3$ substituent is selected from the group consisting of: paraffinic alkyl containing from 1 to about 35 carbon atoms, alkenyl containing from 1 to about 35 carbon atoms; and hydroxy-, alkoxy-, alkoxymethoxy-, and oxo-substituted alkyl and alkenyl containing from 1 to about 20 carbon atoms.

15. The compositions of claim 14 wherein the reaction temperature is between from about 160° C. to about 210° C.

16. The composition of claim 14 wherein the reaction temperature is between from about 170° C. to about 190° C.

17. The composition of claim 14 wherein the (a) and (b) compounds are reacted in stoichiometric proportions.

18. The composition of claim 14 wherein R is an unbranched parafffinic group containing from about 10 to about 20 carbon atoms and R' is selected from the group consisting of methyl and ethyl.

19. The composition of claim 14 wherein the phosphonate compound of (a) is dimethyl octadecyl phosphonate.

20. The composition of claim 14 wherein $R^2$ is a substantially unbranched alkenyl group containing from about 13 to about 21 carbon atoms and $R^3$ is a hydroxy substituted straight chain alkyl group containing from 2 to about 4 carbon alkanes.

21. The composition of claim 14 wherein the imidazoline compound of (b) is 1-(2-hydroxy ethyl)-2-heptadecenyl imidazoline.

* * * * *